(12) United States Patent
Moore et al.

(10) Patent No.: US 7,575,691 B2
(45) Date of Patent: Aug. 18, 2009

(54) METHOD FOR CLEANING CONTAINED BODIES OF WATER

(76) Inventors: David J. Moore, 33 Harare Drive, Borrowdale, Harare (ZW); William C. Betts, W1727 Litchfield Rd., Lake Geneva, WI (US) 53147

( * ) Notice: Subject to any disclaimer, the term of this patent is extended or adjusted under 35 U.S.C. 154(b) by 202 days.

(21) Appl. No.: 11/881,895

(22) Filed: Jul. 30, 2007

(65) Prior Publication Data

US 2008/0000838 A1 Jan. 3, 2008

Related U.S. Application Data

(63) Continuation of application No. 11/010,911, filed on Dec. 13, 2004, now Pat. No. 7,252,843.

(60) Provisional application No. 60/529,919, filed on Dec. 16, 2003.

(51) Int. Cl.
*C02F 1/50* (2006.01)
*C02F 1/76* (2006.01)

(52) U.S. Cl. .................. 210/709; 210/721; 210/724; 210/754; 210/764

(58) Field of Classification Search .................. 210/709
See application file for complete search history.

(56) References Cited

U.S. PATENT DOCUMENTS

| | | |
|---|---|---|
| 4,781,805 A | 11/1988 | Dahlgren |
| 4,952,398 A | 8/1990 | Tapin |
| 5,149,354 A | 9/1992 | Delaney |
| 5,510,108 A | 4/1996 | Chouraqui |
| 5,609,863 A | 3/1997 | Cox |
| 5,700,377 A | 12/1997 | Cox |
| 5,741,526 A | 4/1998 | Miyata |
| 5,980,727 A | 11/1999 | Putz |
| 6,120,698 A | 9/2000 | Rounds et al. |
| 6,139,756 A | 10/2000 | Fuchs |
| 6,248,369 B1 | 6/2001 | Nier et al. |
| 6,287,450 B1 | 9/2001 | Hradil |
| 6,291,397 B1 | 9/2001 | Wilkins, Jr. |
| 6,297,193 B1 | 10/2001 | Miyata et al. |
| 6,451,209 B1 | 9/2002 | Kaas |
| 6,551,519 B1 | 4/2003 | Hartwig |
| 6,734,140 B2 | 5/2004 | Breau |
| 6,868,830 B1 | 3/2005 | Meyer et al. |
| 7,063,804 B2 | 6/2006 | Landis et al. |
| 7,238,290 B2 * | 7/2007 | Rawat et al. ................. 210/759 |
| 7,252,843 B2 | 8/2007 | Moore et al. |
| 7,465,401 B2 * | 12/2008 | Koska ......................... 210/748 |
| 2005/0147691 A1 | 7/2005 | Rawat et al. |

FOREIGN PATENT DOCUMENTS

WO WO 03/095361 A 11/2003
WO PCT/US2004/041718 4/2005

* cited by examiner

*Primary Examiner*—Peter A Hruskoci
(74) *Attorney, Agent, or Firm*—Lesavich High-Tech Law Group, P.C.; Stephen Lesavich

(57) ABSTRACT

A composition and method for cleaning, sanitizing and maintaining contained bodies of water such as swimming pools, wading pools, fountains, ornamental ponds, etc. The composition includes pre-determined percentages of copper sulfate, zinc sulfate, and aluminum sulfate by weight. The composition and method reduce amounts of chlorine and an amount of labor associated with the cleaning, sanitization and maintenance of contained bodies of water.

8 Claims, 2 Drawing Sheets

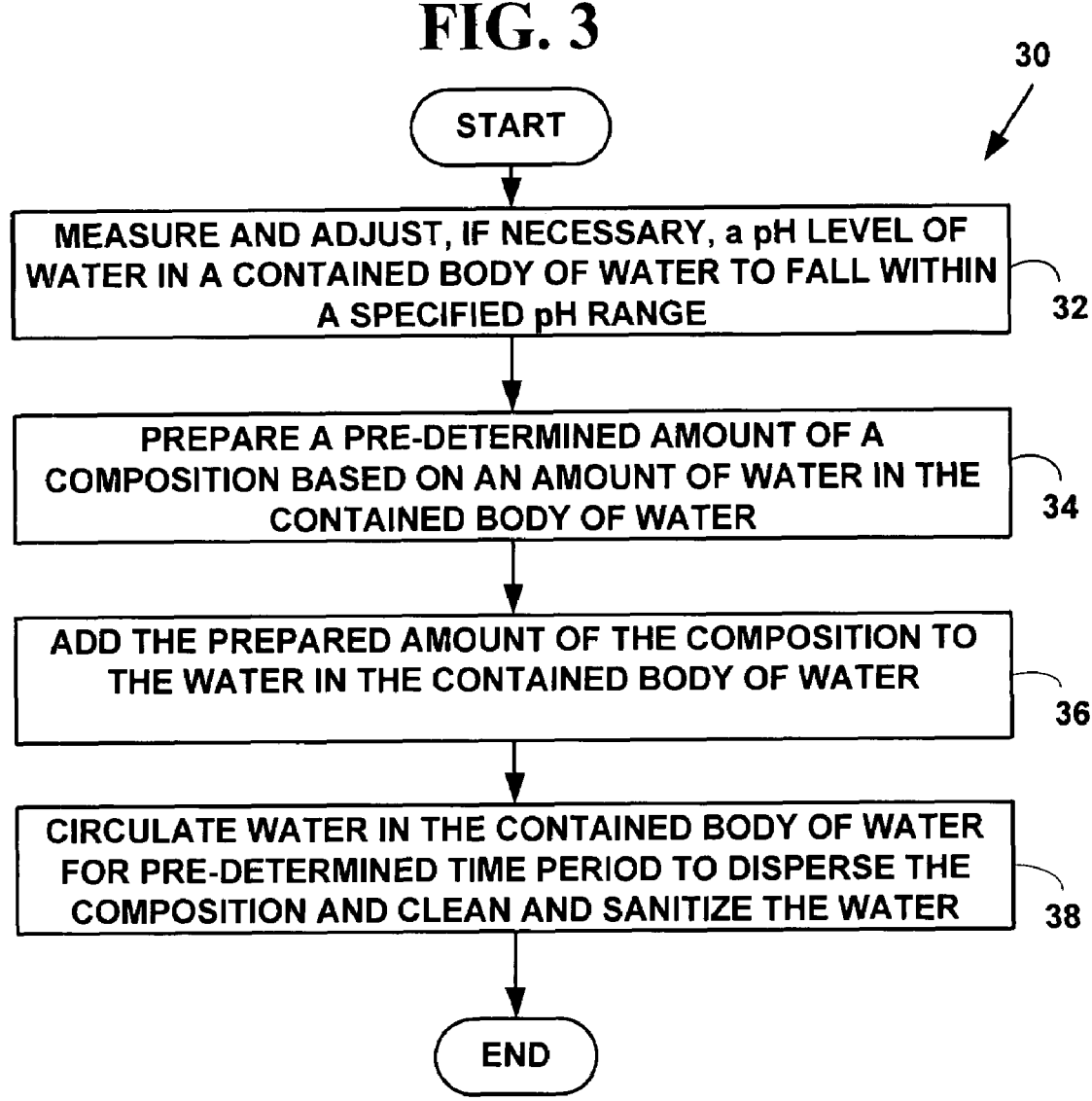

METHOD FOR CLEANING CONTAINED BODIES OF WATER

CROSS REFEFENCES TO RELATED APPLICATIONS

This application is a Continuation of U.S. application Ser. No. 11/010,911 that issued as U.S. Pat. No. 7,252,843 on Aug. 7, 2007, that claims priority to U.S. Provisional Application, 60/529,919 filed Dec. 16, 2003, the contents of all of which are incorporated by reference.

FIELD OF THE INVENTION

This invention relates to a composition and method for cleaning and treating water. More specifically, it relates to a composition and method for reducing an amount of chlorine and an amount of monitoring and maintenance needed for the cleaning and treatment of contained bodies of water.

BACKGROUND OF THE INVENTION

Contained bodies of water such as swimming pools, fountains, ornamental ponds and other contained bodies of water must kept free of microorganisms, and vacuumed or skimmed to keep them clean and free of larger particles and debris. Chlorine is a chemical typically used to sanitize contained bodies of water and reduce or eliminate microorganisms that can be aesthetically unpleasant, hazardous and spread disease. In addition, larger impurities and particulate matter typically must be removed from a contained body of water by skimming the surface of the contained body of water with a net, vacuuming the bottom of the body of water or by filtration.

There are several problems associated with both the use of chlorine and the use of existing methods to keep contained bodies of water free of debris and large particles.

Use of Chlorine (Cl)

Chlorine, when added to a contained body of water in sufficient amounts, kills bacteria and microorganisms by destroying lipids, enzymes and other structures within their cells. This process is known as "oxidation."

When added to a contained body of water, chlorine breaks down into two chemical components: Hypochlorous Acid (HOCl) and one or more hypochlorite ions (OCl). Oxidation occurs more rapidly when there is more Hypochlorous present. The level of each of the Hypochlorous Acid and the Hypochlorite ions depends on a pH level of the contained body of water. As is known in the art, "pH" levels represent how acidic or basic a substance is. The pH scale ranges from 0 to 14. Pure water is "neutral" and has a pH of 7. When chemicals are mixed with pure water, the mixture either stays neutral or becomes either acidic (less than pH 7.0) or basic (greater then pH 7.0)

Hypoclorous Acid and Hypochlorite ions independently accomplish oxidation, but the Hypochlorous Acid typically oxidizes microorganisms quickly (e.g., in several seconds) while the Hypochlorite ion typically takes much longer (e.g., about 30 minutes) to accomplish the same result.

If the pH level of a contained body of water is too high (i.e., too basic), not enough Hypoclorous Acid is produced in the chemical breakdown process. Oxidation sufficient to sanitize and clean a contained body of water, for example, takes much longer at basic pH than at more neutral pH levels. Optimally, the pH levels in the contained body of water should be between around seven.

Sunlight typically speeds up the chemical break down and neutralization of chlorine. To maintain hygienic conditions in a contained body of water over time, chlorine must be continually added to the water as it breaks down.

While the bacteria-killing properties of chlorine are very useful and well established, there are many disadvantages associated with the use of chlorine. Chlorine causes itching and burning of the skin on humans. Chlorine may also exacerbate common existing skin conditions such as eczema. Chlorine frequently causes irritation to the eye and other membranes. Chlorine also has a distinctive odor that may be perceived as unpleasant. Extremely high amounts of chlorine gas in an area surrounding a contained body of water have been associated with certain types of breathing problems. The Hypochlorite ion in chlorine causes damage to fabrics, such as bathing suits.

Chlorine and its chemical components must be continuously added and pH levels of a contained body of water must be carefully monitored to maintain safe levels of both the chlorine and of microorganisms. High amounts of chlorine, due to improper monitoring of pH levels can cause chemical burns and injury to eyes, nose and throat membranes. Inadequate amounts of chlorine can result in a proliferation of bacteria and microorganisms associated with the spread of illness. The monitoring of chlorine levels is a laborious task. Costs associated with the use of chlorine in publicly and privately maintained bodies of water include not only the chemical itself, but also labor costs necessary to monitor and maintain the chlorine and pH balance in the contained body of water.

In response to the problems associated with high levels of chlorine and its monitoring, there have been many attempts to develop alternatives to reduce the amount of chlorine required in swimming pools. One attempted solution has been U.S. Pat. No. 6,551,519 that issued on Apr. 22, 2003, to Hartwig entitled "Ozone of pool water" teaches "a method for the treatment of pool water with ozone at concentrations less than previously employed. Ozonation, as described herein, provides several distinct advantages including but not limited to inactivation of Cryptosporidium and other water borne microorganisms, reduction of combined chlorine concentrations and oxidation of chloramines."

Another attempt is covered by U.S. Pat. No. 6,139,756 that issued on Oct. 31, 2000, to Fuchs entitled "Method of treating swimming pool water" teaches "a method of treating water for a swimming pool comprising chlorination of the water, and filtration of the water using a fixed-bed filter with periodic backflushing of the filter using wash water to which a disinfectant has been added. The disinfectant is a peroxycarboxylic acid with one to six carbon atoms is used as disinfectant, preferably a solution containing peroxyacetic acid and/or peroxyformic acid and hydrogen peroxide. The method results in an improvement of the quality of the swimming-pool water and of the used wash water"

Yet another attempt to solve the problems of high chlorine levels has involved devices making use of electrical current such as U.S. Pat. No. 5,980,727 that issued on Nov. 9, 1999, to Putz entitled "Method and equipment for removing organic halogen compounds from water" teaches "a method to at least extensively remove organic halogen compounds from water or an aqueous solution, at least one magnesium or aluminum anode (1) and at least one associated electrode (2) operating as the cathode dipping into the water. The present invention also concerns equipment with which to implement the method of the invention. Both the method of the invention and the equipment of the invention are preferentially used when disinfecting water with chlorine and in particular in swimming pools."

Use of Metals to Sanitize Contained Bodies of Water

There have also been attempts to solve the problems associated with sanitizing of pools using metals such as copper, silver, zinc and aluminum in compositions or devices to produce a biocide effect. These attempts include U.S. Pat. No. 5,149,354 that issued on Sep. 22, 1992, to Delaney entitled "Composition for treating swimming pools" teaches "a composition for treating swimming pools to inhibit the growth of algae, fungi and bacteria, and to prevent the formation of turbidity in the pool water, more particularly to reduce the dosage of chlorine or chlorine-based chemicals to maintain the pool water in a clear and pathogen-free condition, while at the same time substantially eliminating the risk of deposits and stains being formed on the pool walls, comprises by weight: from about 78 to about 83 percent of copper sulfate, from about 0.08 to about 0.12 percent of silver nitrate, from about 1.0 to about 1.4 percent each of sodium gluconate and zinc chloride or zinc sulfate, from about 16.4 to about 9.6 percent of water, and from about 3.5 to about 4.5 of a complexone, preferably the tetrasodium salt of EDTA. To ensure the desired properties and consistency of the product as well as successful manufacture, the ingredients have to be mixed in a particular manner and sequence of steps."

Another example is U.S. Pat. No. 5,700,377 that issued on Dec. 23, 1997, to Cox entitled "Purification of water" that teaches a "chemical composition for use in purifying water used in swimming pools having surfaces that are comprised of materials that do not react with or dissolve in water, comprising for 2.5 kg of the chemical composition, 1.25 kg of potassiumpersulfate, 300 g of sodium bisulfate, 250 g of ammonium chloride, 100 g of aluminum sulfate, 250 g of sodium bicarbonate, 250 g of calcium chloride and 100 g of ethylendiamine tetra acetic acid (abbreviated EDTA). The potassiumpersulfate and the ammonium chloride are effective in disinfecting water to be purified and in eradicating algae and bacteria therein. The sodium bisulfate, sodium bicarbonate and the calcium chloride are effective in balancing the pH of water to be purified to a pH value within an optimum range between 7.2 and 7.6. The aluminum sulfate serves as a flocculation aid and the copper sulfate is effective in the eradication of black algae. The EDTA is effective to complexing heavy metals in the water."

Additionally, U.S. Pat. No. 4,952,398 issued on Aug. 28, 1990, to Taping entitled "Biocidal composition with copper algicide" that teaches "an improved chemical composition for the treatment of water which is particularly adapted to provide increased biocide activity. By biocide is meant in particular an algacide, a bacetericide and a fungicide. The composition is also suitable for the disinfection of animal breeding places an the cleansing of soil."

There are typically one or more disadvantages associated with previous attempts to solve the problems of cleaning and sanitizing swimming pools. Previous methods, devices and compositions may not effectively reduce the required level of chlorine, may be associated with staining, may be expensive to produce or may lack the oxidizing effect necessary to kill the full range of bacteria. Additionally, these products may not be intended to assist in removing debris and large particles from water, and may rely on separate filtration systems to do so.

Thus, it is desirable to provide a composition and method effective in minimizing the amount of chlorine necessary to maintain hygienic conditions in contained bodies of water. It is also desirable to provide a composition and method that facilitate and reduce the amount of labor required for the removal of particulate matter and larger impurities from contained bodies of water.

Keeping Contained Bodies of Water Free of Debris

Traditional methods used to contained bodies of water clean include vacuuming the debris and particles that sink to the bottom and skimming the floating debris and particles with a net. There is significant labor associated with the two separate operations of vacuuming the bottom of the contained body of water and skimming the surface with a net.

In response to the problems associated with vacuuming and skimming contained bodies of water, there have been many attempts to develop alternatives to reduce the amount of labor required.

These attempts to solve the problems associated with the labor involved in vacuuming and skimming a contained body of water include the development of special nets and improved vacuuming systems. These devices reduce, but do not totally eliminate, the work associated with the separate operations of vacuuming and skimming contained bodies of water. In general, the combined operations of vacuuming and skimming are more labor intensive than the operation of solely vacuuming particles and debris that sink and accumulate at the bottom of the contained body of water.

Other attempts to solve this problem include devices that continuously circulate water through a filtering system. However, these devices are slow and ineffectual for the large amount of water in most contained bodies of water, and often require vacuuming and skimming in conjunction with their use.

For example, U.S. Pat. No. 6,451,209 that issued on Sep. 17, 2002 to Kaas entitled "A method and system for the treatment of water" teaches "a method and a system for purifying bathing water for a swimming pool (1), water is passed through a filter (2) for filtration of the water. A subflow (6) of the filtered water on the downstream side of the filter is passed through a UV system (3) for photochemical treatment. A second subflow (7) of photochemically treated water is withdrawn from the first subflow (6) for nanofiltration or reverse osmosis treatment in a membrane filter device (4). The invention makes it possible to remove carcinogenic substances, such as THM and AOX from the water. A method according to the invention may also be used for removing biocides, pesticides and peroxides, in order to prepare water for drinking."

Another attempt for a pool cleaning device using electrical current is covered by U.S. Pat. No. 6,287,450 that issued on Sep. 11, 2001 to Hradril entitled "Apparatus and method for purifying water with an immersed galvanic" teaches a "a water purification system and method suitable for use in swimming pools, spas, hot tubs, water storage tanks, wells and water cooling towers employs a galvanic cell having a silver or copper or zinc anode electrically connected to a cathode made from a metal of still higher electrochemical potential, normally a platinum group metal and preferably palladium. A galvanic cell of some tens of square centimeters in size and some hundreds of grams in weight liberates sufficient silver or copper ions so as to treat a multi-thousand liter body of water, such as a swimming pool, for, typically under normal contamination, some months until the anode is consumed. Copper and/or silver ions liberated from the galvanic cell suppress bacterial, fungal and/or algae growth, thus, significantly reducing the amount of chlorine, bromine or other chemicals needed to maintain water quality. The invention operates on the current generated by the galvanic action between the dissimilar metals of the anode and cathode, and does not require external electrical power."

U.S. Pat. No. 4,781,805 that issued on Nov. 1, 1998 to Dahlgren entitled "Method for controlling pollution and reducing calcium concentration in aqueous bodies" teaches "a method of an improved method of controlling algal and bacterial pollution, as well as reducing the concentration of dissolved calcium, in a swimming pool, without the necessity of adding electrolytes thereto, involving the steps of: (a) conveying a stream of water from the swimming pool to an enclosed area and back to the pool; (b) providing a pair of spaced-apart electrodes in the enclosed area through which the water is to pass, the electrodes being chemically active and made from mixtures of silver and aluminum alloy containing from about 0.5 to about 5.0 per cent by weight silver and the valance being aluminum alloy; (c) providing a source of alternating electrolytic potential to the electrodes to generate an energy field through the water stream between the electrodes having an rms voltage range from about 25 to about 35 volts and a frequency of alternation of 60 cycles per second to toxify the bacteria and algae in the water and to agglomerate the dissolved calcium into filterable agglomerates; and, (d) providing a filter downstream from the electrodes in the enclosed area for filtering the water as it passes from the electrodes and before it returns to the swimming pool."

Thus it desirable to provide a composition and method of use to solve some of the problems associated with the use of chlorine to disinfect the water in contained bodies and the keeping contained bodies of water free of particles and debris.

SUMMARY OF THE INVENTION

In accordance with preferred embodiments of the present invention, some of the problems associated with the use of chlorine to disinfect the water in contained bodies and keeping water free of particles and debris are overcome. A composition and method for disinfecting and cleaning the water in contained bodies of water is presented.

The composition and method may allow the use of reduced levels of chlorine and reduced labor time to maintain contained bodies of water. The composition comprises 40%-50% copper sulfate, 40%-50% zinc sulfate and 10%-20% aluminum sulfate by weight. The composition and method reduce amounts of chlorine and an amount of labor associated with the cleaning, sanitization and maintenance of contained bodies of water such as swimming pools, wading pools, fountains ornamental ponds and other types of contained bodies of water.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 3 is a flow diagram illustrating a method for cleaning a contained body of water.

DETAILED DESCRIPTION OF THE INVENTION

Exemplary Water Cleaning System

Figure 1:
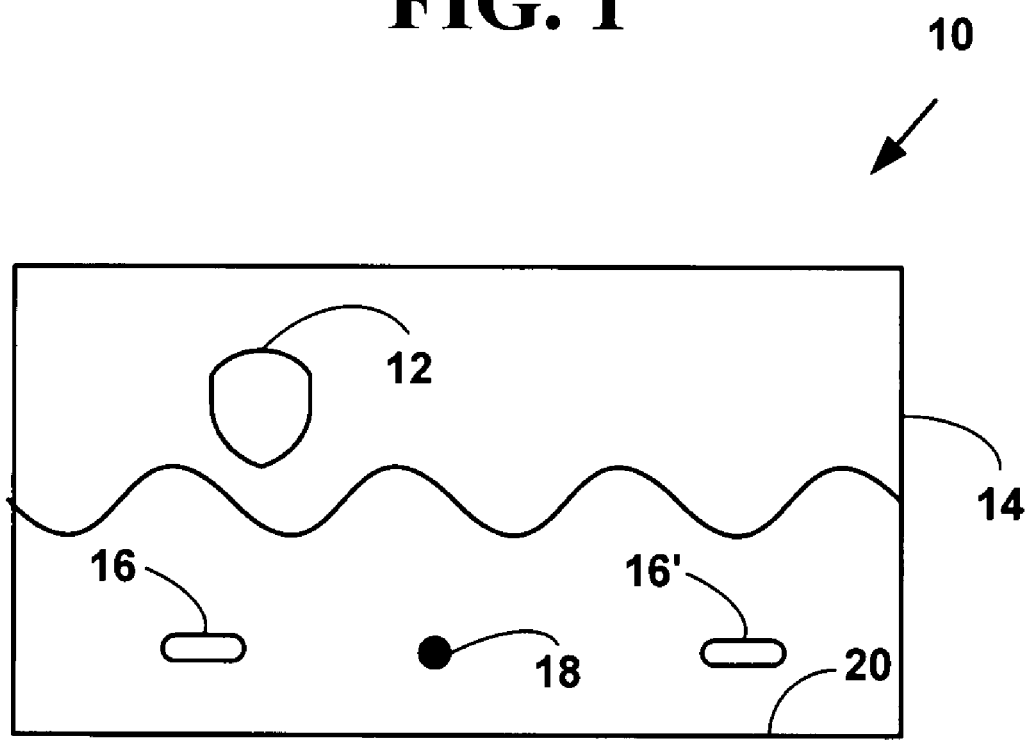
FIG. 1 is a block diagram illustrating an exemplary water cleaning system.

FIG. 1 is a block diagram illustrating an exemplary water cleaning system 10. A composition 12 is added to a contained body of water 14 (e.g., swimming pool, wading pool, fountain, ornamental pond, etc.) to sanitize the water and maintain its chemical properties within pre-determined limits. The composition 12 helps kill and reduce to safe levels any microorganisms 16, 16' that are present in the water 14. The composition 12 also causes debris and other particulate matter 18 to sink to a bottom 20 of the contained body of water 14 for easy removal (e.g., by vacuuming). The composition 12 also causes an amount of chlorine added to the contained body of water 14 to be reduced. However, the present invention is not limited to a water cleaning system with the described components and more or fewer components can also be used to practice the invention.

Exemplary Composition for Cleaning and Sanitizing Contained Bodies of Water

Figure 2:
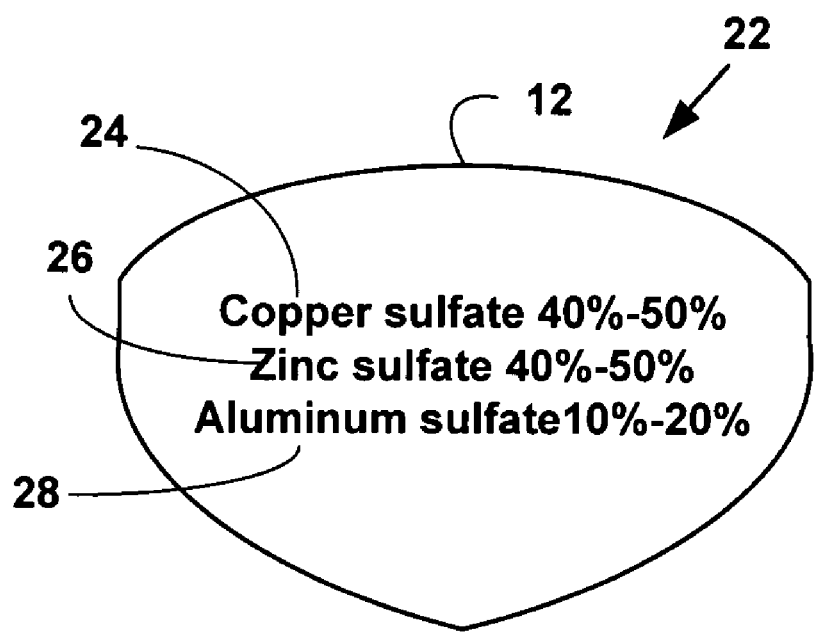
FIG. 2 is a block diagram illustrating chemical ingredients of a composition for cleaning contained bodies of water.

FIG. 2 is a block diagram 22 illustrating chemical ingredients of a composition 12 for cleaning water in contained bodies of water 14. In one embodiment of the present invention, the composition 12 comprises a solid including 40%-50% copper sulfate $CuSO_4$ (24), 40%-50% zinc sulfate $ZnSO_4$ (26) and 10%-20% aluminum sulfate $Al_2(SO_4)_3$ (28) by weight. The composition 12 may further include such other ingredients as may be known in the art to allow increase the solubility of the composition 12, effect combination of the above stated ingredients in a stable, solid format. The percentages of the copper sulfate, zinc sulfate and aluminum sulfate can also be calculated and determined other than by weight of the composition 12. The copper sulfate 24, zinc sulfate 26 and aluminum sulfate 28 may be in naturally occurring forms (e.g., raw mined format) or in a format made in a laboratory.

In one embodiment, the composition 12 is a solid powder format. However, the composition 12 is not limited to a solid powder format and may also include other solid formats including tablet, cake, soluble beads, or a liquid format or other appropriate liquid or solid to including the composition 12.

In one preferred exemplary embodiment of the present invention, the composition 12 includes 45% copper sulfate (24), 45% zinc sulfate (26) and 10% aluminum sulfate (28). However, the present invention is not limited to such an embodiment other of percentages of these ingredients can also be used.

In another exemplary embodiment, the composition 12 may include also include copper sulfite, copper oxide, zinc oxide, zinc sulfite, aluminum oxide, aluminum sulfite, and/or calcium hypochlorite and such other ingredients as may be known in the art to allow increase the solubility of the composition 12 and effect combination of the above stated ingredients into a stable solid format. However, the copper sulfate 24, the zinc sulfate 26 and the aluminum sulfate 28 are still used in the percentages described above. The copper sulfite and other compositions just described could be naturally occurring compositions or those made in a laboratory.

The presence of copper sulfate 24 operates as a biocide agent to inhibit the growth of microbes, algae, fungi and other biological entities thus enabling sanitizing of contained bodies of water 14 using lesser amounts of chlorine than would otherwise be necessary to sanitize water. The copper sulfate 24 additionally operates to inhibit photo-degradation of the chlorine from sunlight thereby further reducing the amount of chlorine necessary to sanitize the contained body of water 14. This eliminates some of the problems associated with use of higher levels of chlorine in contained bodies of water.

The copper sulfate 24 is used in composition 12 in a percentage based on weight, ranging from 40% to 50%. The exact percentage used depends upon the source of the copper sulfate 24 and its solubility in the water to be treated. Copper sulfate 24 can be provided by any suitable copper-containing material known to produce copper sulfate, which dissolves in aqueous solutions at the expected temperature and pH of the water to be treated.

Zinc sulfate 26 is also used in composition 12 in a percentage based on weight, ranging from 40% to 50%. The exact percentage of zinc sulfate 26 used is also dependent upon the source of zinc sulfate 30 and its solubility in the water to be treated.

The zinc sulfate 26 operates in conjunction with the copper sulfate 24 and aluminum sulfate 28, while maintaining levels copper sulfate 24 that are low enough to prevent significant staining of surfaces of a contained body of water, and further inhibits biodegradation of chlorine. Zinc sulfate 26 can be provided by any compound known to yield zinc sulfate 30 in aqueous solution at the expected pH and temperature of the water to be treated.

In the present invention, aluminum sulfate 28 is used in a percentage amount by weight based upon the total composition, ranging from 10% to 20%. The exact percentage of aluminum sulfate is determined by the particular source of aluminum sulfate 28 and its solubility in the water to be treated. The aluminum sulfate 28 can be provided by any suitable compound that releases aluminum sulfate 28 which dissolves in an aqueous solution at the expected pH and temperature of the water to be treated.

In addition, more or fewer ingredients may be used in the composition 12 depending on an amount of contained water 14 to be cleaned, the pH level of the water to be cleansed and sanitized, the purity of the ingredients included in the composition 12 and other factors such as water temperature, etc.

Exemplary Method for Cleaning and Sanitizing Contained Bodies of Water

FIG. 3 is a flow diagram illustrating a Method 30 for cleaning a contained body of water. At Step 32 a pH level of water in the contained body of water 14 is measured and adjusted if necessary, to fall within a specified pH range. At Step 34, a pre-determined amount of a composition 12 is prepared based on an amount of water in the contained body of water 14. At Step 36, the prepared amount of composition 12, is added to the water of the contained body of water. At Step 38, the water is circulated in a contained body of water 14 for a pre-determined amount of time to disperse the composition to clean and sanitize the water.

Method 30 is illustrated with an exemplary embodiment. However, the present invention is not limited to such an embodiment and other embodiments can also be used to practice the invention.

In such an exemplary embodiment of Method 30, at Step 32, a pH level of the water in a contained body of water 14 is measured and found to be in an appropriate range, or in the range of pH about 7.0 to 7.6. If the pH is out this range, it is adjusted to a pH between about 7.0 and 7.6.

At Step 34, if the composition 12 is in solid format, a pre-determined amount of the composition 12 is prepared based on an amount of water in the contained body of water by dissolving it in a pre-determined amount of water or other suitable solvent. If the composition 12 is in a liquid format, no dissolving is necessary. The preparation simply includes opening a container including the composition 12 in liquid format and pouring out the pre-determined amount.

In one preferred exemplary embodiment of the invention, about the pre-determined amount of the composition include about one (1) pound of the composition 12 for about 10,000 gallons of water wherein the composition 12 comprises 45% copper sulfate (24), 45% zinc sulfate (26) and 10% aluminum sulfate (28). However, the present invention is not limited to this exemplary embodiment and other pre-determined amounts of the composition 12 added to other pre-determined amounts of water can also be used to practice the invention.

An amount of composition 12 used is dependent on the exact percentages of copper sulfate, zinc sulfate and aluminum sulfate used in the composition 12, as well as a pH of the water and the amount of chlorine in the water and varying amounts of the composition 12 can be used to practice the invention.

To determine an amount of water in gallons in a rectangular pool, with a varying depth, a volume in cubic feet is first determined. Equation 1 can be used to determine a pool volume in cubic feet of a rectangular pool that varies in depth from a shallow end to a deep end:

Rectangular pool volume in cubic feet=((Shallow end depth+deep end depth)/2)*length*width)  (1)

The number of gallons of water a pool holds can be determined by Equation 2:

Gallons of water a pool holds=pool volume in cubic feet*7.5 gallons of water per cubic foot  (2)

For example, a rectangular pool is fourteen feet in width by twenty-four feet in length with a depth of three feet at the shallow end and five and one half feet at the deep end. Table 1 illustrates an amount of water in gallons this exemplary pool holds using Equations 1 and 2 to calculate gallons of water.

TABLE 1

((3' + 5.5')/2) * 24' * 14') = 1428 cubic feet
1428 cubic feet * 7.5 gallons of water per cubic foot = 10,710 gallons of water.

Other math equations known in the art are used to determine the number of gallons of water a contained body of water holds is dependent on a size and shape of the contained body of water.

At Step 36, the pre-determined amount of the composition 12 is added to the contained body of water 14. At Step 38, the water is circulated in the contained body of water 14 using a water filter, pump or other water circulating device to disperse the composition 12 and clean and sanitize the body of water.

The composition 12 and Method 30 helps kill and reduce to safe levels any microorganisms 16, 16' that are present in the contained body of water 14. The composition 12 causes debris and other particulate matter 18 to sink to the bottom 20 of the contained body of water 14 for easy removal (e.g., by vacuuming).

The composition 12 and Method 30 causes the amount of chlorine a contained body of water 14 to be reduced. The composition 12 and Method 30 may be used for contained bodies of water 14, such as pools, fountains, ornamental ponds, etc. including water to which chemicals (e.g., chlorine) have been already added (e.g., water obtained from a city pipeline or faucet, etc.).

However, the present invention is not limited to such contained bodies of water and may also be used for larger bodies of water such as lakes, etc. that also include natural occurring water.

It should be understood that the compositions methods and system described herein are not related or limited to any particular type of chemical component unless indicated otherwise. Various combinations of general purpose, specialized or equivalent chemicals and components and combinations thereof may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more fewer or equivalent elements may be used in the block diagrams and compositions.

While various elements of the preferred embodiments have been described as being a solid, in other embodiments liquids may alternatively be used, and vice-versa.

The claims should not be read as limited to the described order or elements unless stated to that effect. In addition, use of the term "means" in any claim is intended to invoke 36 U.S.C. §112, paragraph 6, and any claim without the word "means" is not so intended.

Therefore, all embodiments that come within the scope and spirit of the following claims and equivalents thereto are claimed as the invention.

We claim:

1. A method cleaning and sanitizing a contained body of water sanitized with chlorine, comprising:
    measuring a pH level of water in the contained body of water;
    adjusting the measured pH, if necessary, to fall within a specified pH range;
    preparing a pre-determined amount of a composition based on an amount of water in the contained body of water, wherein the composition comprises 40% to 50% copper sulfate, 40% to 50% zinc sulfate; and 10% to 20% aluminum sulfate, by weight;
    adding the prepared amount of composition to the water of the contained body of water; and
    circulating the water in the contained body of water for a pre-determined amount of time is disperse the composition, thereby cleaning and sanitizing the water in the contained body of water,
    wherein the composition cleans and sanitizes the water in the contained body of water, inhibits photo-degradation of any chlorine added to the water from sunlight thereby further reducing an amount of chlorine necessary to sanitize the water in the contained body of water, maintains the chemical properties of the water within pre-determined pH limits and causes debris and other particulate matter to sink to a bottom of the water for easy removal.

2. The method of claim 1 wherein the specified pH range is 7.0 to 7.6.

3. The method of claim 1 wherein the composition further comprises 45% copper sulfate, 45% zinc sulfate; and 10% aluminum sulfate, by weight.

4. The method of claim 1 wherein the pre-determined amount of the composition includes one pound of the composition for about every 10,000 gallons of water.

5. The method of claim 1 wherein the contained body of water includes swimming pools, wading pools, fountains or ornamental ponds.

6. The method of claim 1 wherein the pre-determined amount of the composition is prepared by dissolving it in a suitable solvent for adding to the contained body of water in a liquid format.

7. The method of claim 1 wherein the pre-determined amount of the composition is in solid format including a powder, tablet, cake or soluble beads added to the contained body of water.

8. The method of claim 1 wherein the debris and other particulate matter is removed from the bottom via vacuuming.

* * * * *